United States Patent [19]
Steer

[11] Patent Number: 5,979,449
[45] Date of Patent: Nov. 9, 1999

[54] ORAL APPLIANCE DEVICE AND METHOD FOR USE THEREOF FOR APPETITE SUPPRESSION

[76] Inventor: Eugene Lyle Steer, 2500 N. Hayden Rd., #20, Scottsdale, Ariz. 85257

[21] Appl. No.: 09/058,622

[22] Filed: Apr. 9, 1998

[51] Int. Cl.$^6$ ....................................................... A61F 5/56
[52] U.S. Cl. ................................ 128/848; 128/861; 433/6
[58] Field of Search ..................................... 128/848, 859, 128/860, 861, 862; 433/6, 215, 229

[56] References Cited

U.S. PATENT DOCUMENTS

| | | |
|---|---|---|
| 3,132,647 | 5/1964 | Corniello . |
| 3,224,442 | 12/1965 | Stubbs . |
| 4,471,771 | 9/1984 | Steven et al. . |
| 4,669,459 | 6/1987 | Spiewak et al. . |
| 5,277,202 | 1/1994 | Hays ........................................ 128/848 |
| 5,381,783 | 1/1995 | Hintz ....................................... 128/861 |
| 5,467,783 | 11/1995 | Meade . |
| 5,592,951 | 1/1997 | Castangnaro et al. . |
| 5,624,257 | 4/1997 | Farrell ..................................... 128/861 |
| 5,715,840 | 2/1998 | Hall ......................................... 128/848 |

*Primary Examiner*—Nicholas D. Lucchesi
*Attorney, Agent, or Firm*—Harry M. Weiss; Jeffrey Weiss; Paul W. Davis

[57] ABSTRACT

An oral appliance device and method are provided for suppressing the appetite for weight control. The oral appliance device includes a substantially U-shaped channel for receiving the upper teeth of the wearer and a roof portion that conforms to the roof of the wearer's mouth. The roof portion includes an upwardly protruding rear tab portion that contacts the roof of the mouth substantially at the juncture between the soft and hard palates. A lower surface of the roof portion contacts a top surface of the tongue at substantially a rear portion thereof. The method includes fitting the oral appliance device to the wearer's mouth by deforming the device by hot water or the like to conform to the wearer's mouth and then cooling it down, inserting the fitted device in the mouth such that the upper teeth are received in the channel and the upwardly protruding rear tab portion contacts the roof of the mouth and the roof portion lower surface contacts the tongue.

8 Claims, 1 Drawing Sheet

ORAL APPLIANCE DEVICE AND METHOD FOR USE THEREOF FOR APPETITE SUPPRESSION

FIELD OF THE INVENTION

The present invention relates generally to a weight control device and method and more particularly to an oral appliance device and method thereof for appetite suppression.

BACKGROUND OF THE INVENTION

Weight control is a concern for many. If not sufficiently controlled, obesity may result. The cause of obesity is simple—consuming more calories than are expended as energy. There are arguably many ways to control weight and thus treat obesity, for example, diet, medications, physical activity, surgery, jaw wiring, behavior modification, and self-help organizations. None of these methods is entirely effective and some are dangerous. It is recognized that no simple or generally effective therapy exists. Obesity is a chronic condition resistant to treatment and prone to relapse.

There have been several prior oral appliances, which attempt to aid the wearer in controlling weight. Stubbs, U.S. Pat. No. 3,224,442 describes a combined weight repulsing and cigarette reneging oral appliance. The Stubbs appliance includes a pair of long oval relatively thin longitudinally and transversely curved members connected by an elastic band to which is hung a small button or tab. The appliance is inserted in front of and against the lower teeth inside the lips and cheeks. The small button or tab extends rearwardly between lower incisor teeth to the tongue for frivolous movement to stimulate the flow and swallowing of saliva to satisfy the desire for food or cigarettes. Brown et al., U.S. Pat. No. 4,471,771 describes an oral appliance as an alternative to jaw wiring. The Brown et al. appliance is described in one embodiment as including a guard having meshed openings pivotally mounted to an upper support brace configured to fit against the roof of the user's mouth. The brace may be secured by looping the ends thereof around upper rear teeth. The guard functions as a sieve allowing liquids and finely ground materials to pass therethrough, yet blocking or preventing solid foods having a size larger than the openings from passing therethrough. The Brown et al. appliance is therefore not an appetite suppression device. Neither of these prior devices suppresses appetite by applying pressure to the roof of the mouth and the upper surface of the tongue.

Accordingly, there has been a need for a novel oral appliance device which effectively suppresses appetite. There is also a need for an appetite suppressing oral appliance device that can be worn without substantial discomfort and interference with speech. Additionally, a need exists for a weight control device and method that are safe and can decrease the appetite in a healthy manner. A need also exists for a device and method to help develop self control to modify eating habits without the use of medication, which leads to more likely permanent and healthy weight loss. The present invention fulfills these needs and provides other related advantages.

SUMMARY OF THE INVENTION

Accordingly, it is an object of this invention to provide an oral appliance device and method that effectively suppress the appetite.

It is also an object for an appetite suppressing oral appliance device and method that can be used without substantial discomfort and interference with speech.

It is a further object for an appetite suppressing oral appliance device and method that are safe and can decrease the appetite and control weight in a healthy manner.

It is a still further object for an appetite suppressing oral appliance device and method to help people develop self control to modify eating habits without the use of medication which leads to more likely permanent and healthy weight loss.

The present invention resides in an improved oral appliance device and method for suppressing a wearer's appetite by applying pressure to the roof of the mouth and the tongue and by increasing salivation. The oral appliance device comprises, generally, a substantially U-shaped channel adapted to receive the wearer's upper teeth and a roof portion including an upwardly protruding rear tab portion and a lower surface that respectively applies pressure to the roof of the mouth and the tongue to suppress the appetite.

The roof portion includes a raised substantially central portion. The posterior edge of the raised substantially central portion terminates in the upwardly protruding rear tab portion. The upwardly protruding rear tab portion contacts the roof of the mouth substantially at the juncture between the hard and soft palates. The roof portion lower surface engages a top surface of the wearer's tongue at a rear portion thereof.

In the method of the invention, the oral appliance device is custom fitted in the mouth of the wearer by heating the device by hot water or the like to slightly soften the oral appliance so it may be slightly deformed to conform to the wearer's mouth and then cooled. After one fitting, the oral appliance may be worn at the wearer's convenience for appetite suppression.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
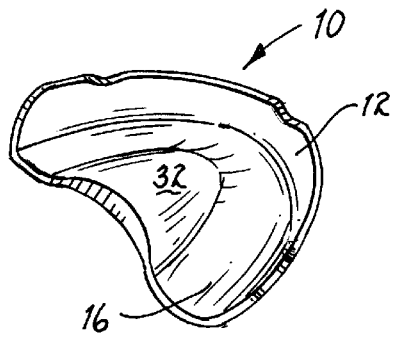
FIG. 1 is a perspective view of an appetite suppressing oral appliance device embodying the invention, illustrating a substantially U-shaped channel and a roof portion including a raised substantially central portion.
Figure 2:
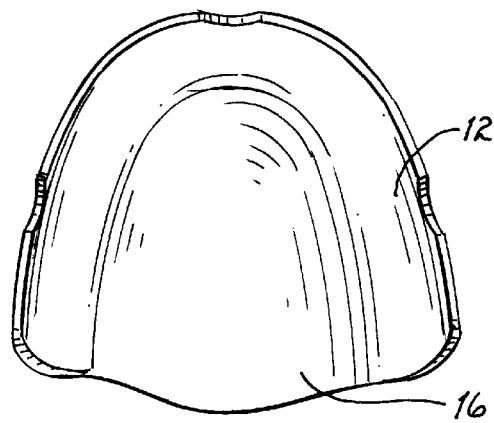
FIG. 2 is a top view of the device of FIG. 1.
Figure 4:
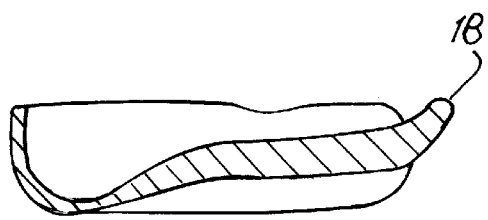
FIG. 4 is a sectional view of the oral appliance device taken generally along the line 4—4 of FIG. 3.

As shown in the drawings for purposes of illustration, the present invention is concerned with an improved oral appliance device and method for weight control, the device generally designated in the accompanying drawings by the reference number 10. The oral appliance device 10 comprises, generally, a channel 12 adapted to receive a wearer's upper teeth 14, a roof portion 16 that includes an upwardly protruding rear tab portion 18 and a lower surface 20 that respectively applies pressure to the roof 22 of the mouth and the tongue 24 to suppress the appetite.

The channel 12 is substantially U-shaped to receive the upper teeth 14 and defined by a substantially arcuate sidewall 26 and a floor 28.

The roof portion 16 includes an upper surface 30 that is worn against a substantial portion of the roof 22 of the mouth or palate. The lower surface 20 contacts a rear portion of a top surface of the tongue 24. The palate is the roof of the mouth consisting of an anterior bony portion (hard palate) and a posterior muscular portion (soft palate) that separate the oral cavity from the nasal cavity.

Figure 3:
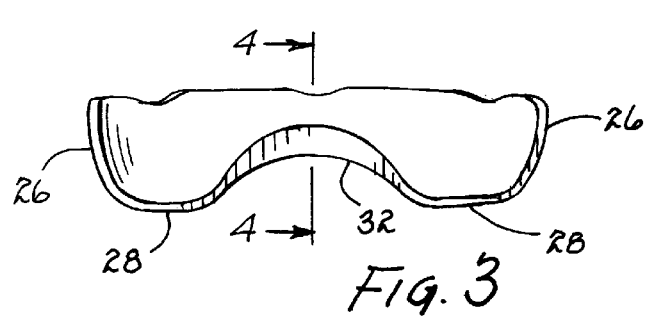
FIG. 3 is a rear view of the device of FIG. 2, illustrating the raised portion substantially in the center of the roof portion with the substantially U-shaped channel on the outside thereof.

As shown in FIG. 3, the roof portion 16 includes a raised curved substantially central portion 32 that terminates posteriorly in the upwardly protruding rear tab portion 18. The raised curved substantially central portion 32 substantially conforms to the superior dental arch (not shown) formed by the upper teeth 14 such that the roof portion 16 covers a substantial portion of the roof 22 of the mouth.

The upwardly protruding rear tab portion 18 protrudes upwardly at approximately a 45-degree angle from the posterior edge of the raised curved substantially central portion 32. The upwardly protruding rear tab portion 18 is relatively short extending about ⅛ inch above the raised curved substantially central portion 32 to contact substantially the junction (not shown) between the hard and soft palates.

The appliance 10 is preferably composed of a mouthguard material, such as acrylic resin or the like. The material is preferably resilient such as stiff plastic or rubber. The device is made during an injection molding process. The resilience of the mouthguard material permits custom fitting by the wearer.

Figure 5:
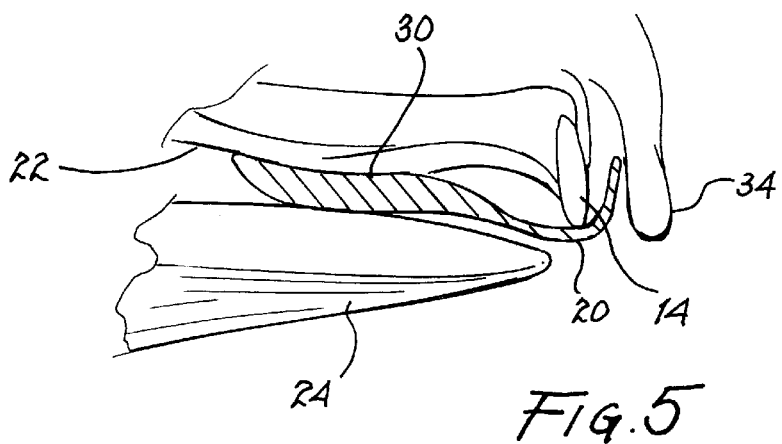
FIG. 5 is a environmental view, illustrating the device as worn inside the mouth with an exemplary upper tooth received in the substantially U-shaped channel, and the raised substantially central portion of the roof portion terminating at the posterior edge in an upwardly protruding rear tab portion that contacts the roof of the mouth and a lower surface of the roof portion contacting a top surface of the tongue.

Prior to wearing the device 10, the wearer runs the device 10 under hot water to permit deformation of the device. The device 10 is then inserted into the wearer's mouth with the upper teeth 14 received in the substantially U-shaped channel 12 with the side wall 26 of the channel 12 between the wearer's lip 34 and the teeth 14 as shown in FIG. 5. The device 10 should be worn such that the upwardly protruding rear tab portion 18 contacts substantially the junction between the hard and soft palates and the lower surface 20 of the roof portion 16 contacts the rear portion of the top surface of the tongue 24 when the mouth is closed. When the device 10 cools, a custom fit is acquired. For subsequent wearings, the device need only be inserted into the mouth i.e. no further fitting is required. The device leaves the tongue and lower jaw substantially free. It is believed that continued use of the device 10 along with continued initiation of the gag reflex and increased salivation occasioned by the upwardly protruding rear tab portion 18 and tongue 24 contact suppresses the appetite.

Although a particular embodiment of the invention has been described in detail for purposes of illustration, various modifications may be made without departing from the spirit and scope of the invention. Accordingly, the invention is not to be limited, except as by the appended claims.

I claim:

1. An oral appliance for suppressing a wearer's appetite comprising in combination:

a channel adapted to receive the wearer's upper teeth; and a roof portion including a raised substantially central portion that terminates at a posterior edge in an upwardly protruding rear tab portion dimensioned to contact the roof of the mouth substantially at the juncture between the hard and soft palates to suppress the wearer's appetite.

2. The oral appliance of claim 1 wherein the roof portion has a lower surface for contacting a top surface of the wearer's tongue at a rear portion thereof to further suppress the wearer's appetite.

3. The oral appliance of claim 1 wherein the channel is substantially U-shaped.

4. The oral appliance of claim 1 wherein the upwardly protruding rear tab portion protrudes upwardly from the posterior edge of the raised substantially central portion at approximately a 45-degree angle.

5. The oral appliance of claim 1 wherein the posterior edges of the raised substantially central portion and the channel are substantially coterminous.

6. A method of suppressing the appetite for weight control in a person comprising the steps of:

fitting an oral appliance to the mouth of a person who wants to control his or her weight;

inserting the fitting oral appliance into the person's mouth such that his or her upper teeth are received in a substantially U-shaped channel of the oral appliance; and adjusting the fitted oral appliance until an upwardly protruding rear tab portion at a posterior edge of a raised substantially central portion of a roof portion of the oral appliance comfortably contacts the roof of the mouth substantially at the juncture between the hard and soft palates to suppress the appetite.

7. The method of suppressing the appetite for weight control of claim 6 wherein fitting the oral appliance comprises deforming the oral appliance by heat to conform to the person's mouth and then cooling the oral appliance to create the fitted oral appliance.

8. The method of suppressing the appetite for weight control of claim 6 wherein the roof portion has a lower surface for contacting a top surface of the person's tongue at a rear portion thereof to further suppress the wearer's appetite.

* * * * *